United States Patent [19]

Vincent

[11] Patent Number: 4,592,741

[45] Date of Patent: Jun. 3, 1986

[54] MEDICAL APPARATUS DESIGNED FOR THE ASPIRATION OF PHNEUMOTHORAX

[76] Inventor: Michel J. Vincent, 47 rue Tronchet, Lyon 6eme - Rhone, France

[21] Appl. No.: 619,876

[22] Filed: Jun. 12, 1984

[51] Int. Cl.⁴ .............................................. A61M 1/04
[52] U.S. Cl. ....................... 604/35; 604/67; 604/119; 604/118; 73/861.47; 73/861.57
[58] Field of Search .............. 604/118, 119, 140, 146, 604/147, 149, 246, 35, 26, 22, 245, 67; 73/861.44, 861.47, 861.57

[56] References Cited

U.S. PATENT DOCUMENTS

| | | | |
|---|---|---|---|
| 2,140,113 | 12/1938 | Pilling et al. | 604/246 |
| 2,918,917 | 12/1959 | Emerson | 128/204.21 |
| 3,182,500 | 5/1965 | Ishii | 73/861.57 |
| 4,231,366 | 11/1980 | Schael | 604/67 |
| 4,496,342 | 1/1985 | Banko | 604/22 |

FOREIGN PATENT DOCUMENTS

| | | | |
|---|---|---|---|
| 1098676 | 2/1961 | Fed. Rep. of Germany | 604/118 |
| 2438091 | 8/1976 | Fed. Rep. of Germany | 73/861.57 |
| 1025433 | 4/1953 | France | 604/245 |
| 293607 | 10/1971 | U.S.S.R. | 604/245 |

Primary Examiner—Henry J. Recla
Attorney, Agent, or Firm—Remy J. VanOphem

[57] ABSTRACT

A device for the aspiration of an air pocket surrounding a collapsed lung. The device includes a needle to be inserted into the cavity surrounding the collapsed lung, through the ribs of the patient. The needle is connected to a suction pump by means of a hose. A float-type flow-meter is provided to measure the air flow rate through the hose and the suction pump and to transmit an electrical signal which is indicative of the flow rate to an electronic controller which calculates and displays the total volume of the air that has flowed through the sensor. A vent line is provided between the suction pump and the flow-meter to prevent sudden increases in flow rates through the needle, and a three-way valve is provided to control flow through the vent line.

12 Claims, 2 Drawing Figures

4,592,741

MEDICAL APPARATUS DESIGNED FOR THE ASPIRATION OF PHNEUMOTHORAX

BACKGROUND OF THE INVENTION

The present invention relates to a device for the aspiration of an air pocket surrounding a collapsed lung.

A device according to the present invention includes a suction pump which sucks into a hose extended with a hollow needle and a variable vent and a float equipped flow meter which controls the flow through the suction pump and the hose. The flow meter float is connected to a magnetic core, and the core moves with the float inside a fixed induction coil. The signals sensed by the coil are processed by an electronic counter that displays the total volume of air withdrawn from the pneumothorax.

SUMMARY OF THE INVENTION

The present invention pertains to a novel medical device for the aspiration of the pneumothorax.

It is known that some patients suffer from pulmonary collapse. Regardless of its cause, this condition is the result of a lung which collapsed on itself, creating an air pocket, called a pneumothorax, between the lung and the inside wall of the throacic cage. One of the medical treatments for this condition involves the insertion of a hollow needle between the ribs of the patient and the withdrawal of the air from the air pocket through the needle. Generally the air is drawn out until the lung recovers its normal volume, that is until it again makes contact with the pleura. In some cases, however, the draw of an excessive volume of air, or the withdrawal of air at too low a pressure, may cause severe or fatal complications.

Experience shows that satisfactory results can be achieved if the pneumothorax is aspirated without drawing more than a predetermined volume of air, generally from 1000 to 1500 milliliters.

Controlled aspiration of pneumothorax air is usually obtained by using an hydraulically controlled device which operates according to the principle of interconnecting vessels. However, a device of this type has the disadvantage of being cumbersome and uneasy to handle. Consequently, the technique has been abandoned by numerous facilities which are presently using an ordinary vacuum draw, notwithstanding the aforementioned risks.

The aspiration device of the present invention eliminates these disadvantages by offering a relatively simple, inexpensive and easy to handle device for the aspiration of air from the pneumothorax.

The device of the present invention is made up of a suction device, such as a suction pump, and the low pressure side of the suction device is connected to the float of a flow-meter. The float, which floats in the stream of air that flows through the flow-meter, is connected to a magnetic core, and the core is free to move with the float with respect to an induction coil. The induction coil instantaneously senses the float position, which indicates the rate of air flow at any given moment and the induction coil also sends a corresponding signal to an electronic meter which calculates and indicates the total flow.

One of the features of the present invention is that the float-type flow-meter is mounted in series between the suction pump and the hollow aspirator needle.

Another feature of the present invention is that a three-way control or breather valve is connected between the suction pump and the float-type flow-meter, to provide an adjustable vent connected with the atmosphere on the suction line.

According to yet another feature of the present invention, a low pressure gage is provided between the three-way breather valve and the float type flow-meter.

The attached drawing illustrates a preferred embodiment of the present invention, but it is not intended to limit the invention by the drawing.

DETAILED DESCRIPTION OF THE PREFERRED EMBODIMENT

Figure 1:
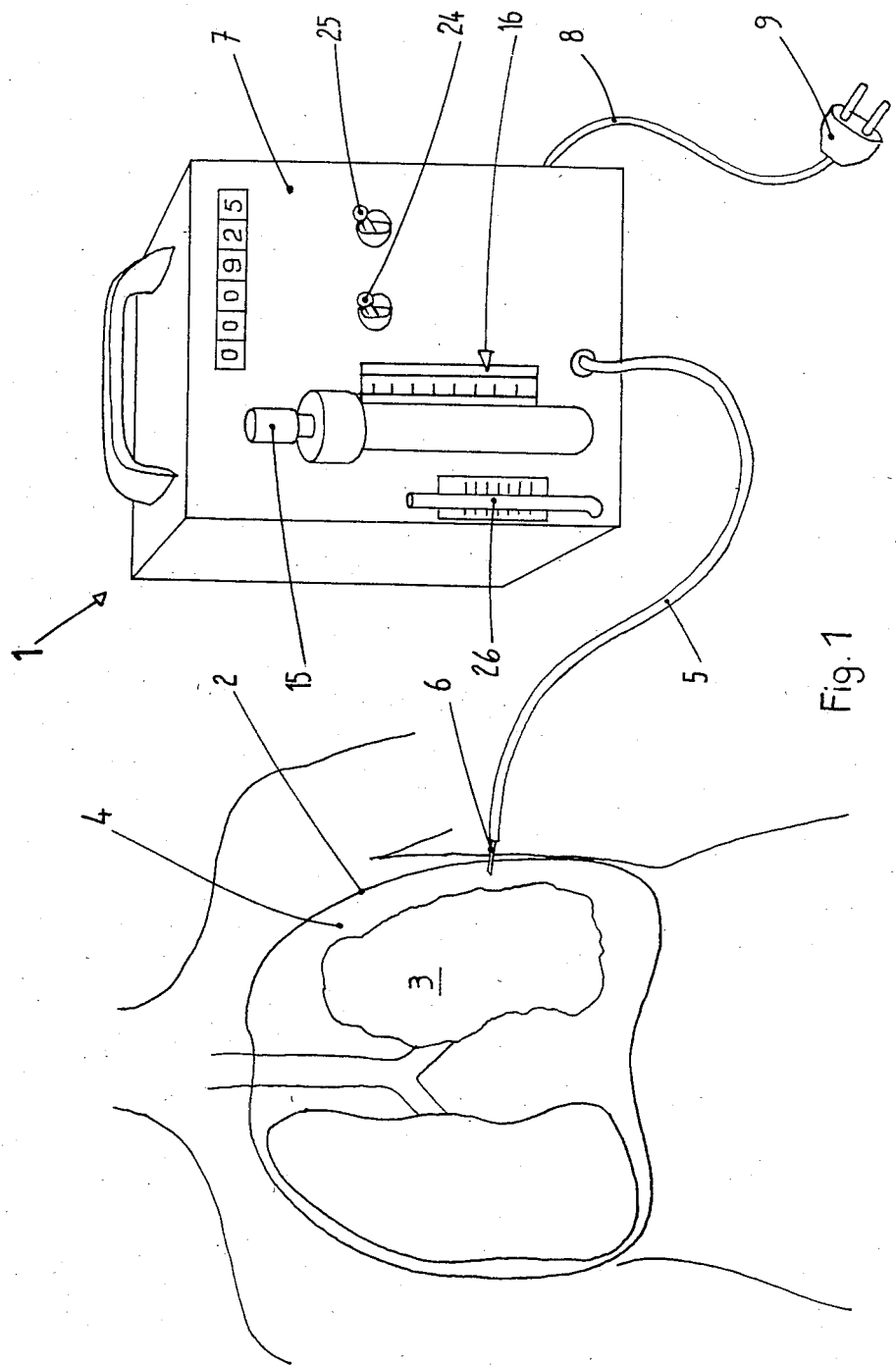
FIG. 1 is a three-dimensional view which illustrates the principle of operation of a preferred embodiment of a medical device according to the present invention.
Figure 2:
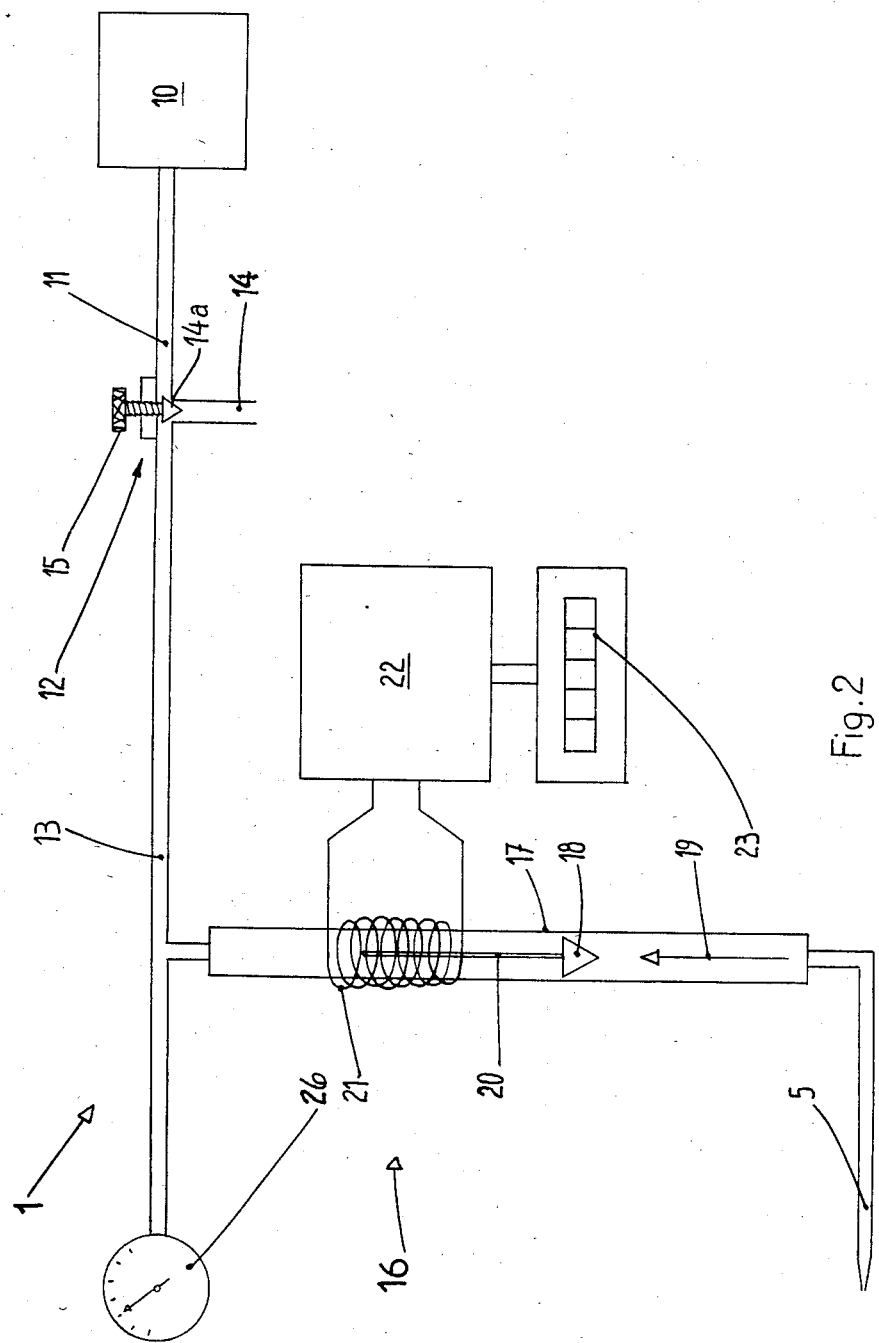
FIG. 2 is a schematic drawing illustrating the control system for controlling the operation of the device of claim 1.

A device 1 according to the present invention, as illustrated in the drawing figures, is shown complete and ready for use in the pulmonary department of a hospital for instance.

FIG. 1 shows a patient in whose thorax 2 the left hand side lung 3 has collapsed. As a result, a large air pocket 4 has developed between the collapsed lung 3 and the pleura which covers the inside of the thorax 2. This condition is commonly called reversed pneumothorax. It is usually corrected by drawing the air from the pocket 4, but in doing so, the operator should be careful and only draw a limited amount of such air, for example, from 1.0 to 1.5 liters.

The device 1 includes, therefore, a hose 5 having a hollow needle 6 that the operator inserts between the ribs and into the thorax 2 of the patient.

The device 1 also includes a solid box 7, and the solid box is provided with an electrical wire 8 including a plug 9.

When the plug 9 is plugged into a suitable source of electrical power, not shown, the power will activate a suction pump 10 allowing for the creation of a partial vacuum inside a hose 11 which is in communication with the suction pump 10. A three-way valve 12 is interposed between the hose 11 and another hose 13. The three-way valve is provided with a breather needle 14a whose position within the valve 12 is controlled by a knurled knob 15, and by the operation of the three-way valve 12 by means of the knurled knob 15, the drain flow through the hose 13 can be controlled at a variable rate.

A pressure gage 26 is mounted at the end of the hose 13, in parallel with the vent 14. For purposes of illustration, as is indicated in FIG. 1, the pressure gage 26 is a mercury gage.

The hose 13 is connected with the upper portion of an air flow-meter 16. The lower part of the air flow-meter opens into hose 5.

The flow-meter 16 includes a rigid pipe 17, which is desirably transparent and within which a float 18, sometimes also called a "diabolo", is provided to float at variable heights in the air flowing through the pipe 17, as schematically indicated by arrow 19.

According to the preferred embodiment of the present invention, the float or diabolo 18 is rigidly mounted with a stem or magnetic core 20 which extends upward from the float. This core is made of a magnetic metal and it constitutes a core which is mobile within an induction coil 21 surrounding the pipe 17.

The induction coil 21 is connected to an electronic meter 22 which processes the signals which it receives and which are related to the motion and instant position of the core nucleus and, therefore, of the float 18.

The electronic meter 22 operates a digital display 23 located on the front of the box 7.

Additionally, two knobs 24 and 25 are provided to respectively control the operating of the suction pump 10 and the electrical operation of the whole device.

The device operates as follows:

After inserting the needle 6 in the thorax 2 of the patient, the operator plugs the apparatus into the electrical outlet and activates the suction pump 10.

The pump draws the air from the pocket 4 through the flow-meter 16, where, at any given moment, the position of the float 18 instantaneously reflects the rate of air flow. The electronic meter 22 receives and processes the information generated in the induction coil 21, with the following results.

The instantaneous air intake is displayed at any given moment.

The cumulative total volume of air drawn from the pocket 4 is displayed in the display box 23.

Finally, as this cumulative volume reaches the predetermined value entered in the memory of the apparatus 1, the pump 10 automatically stops.

Furthermore, the pump 10 is selected so as to generate a low pressure estimated to be approximately 30 cms of water. The air flow intake of the pump is desirably set at between 100 and 400 milliliters per minute with the optimal flow being 300 milliliters per minute.

During the operation, the knurled knob 15 allows the operator to control the value of the pressure drop by adjusting the vent 14.

As a result of the above features, the pump 10 will never be able to intake at a pressure drop exceeding 30 cms of water, even if the flow through the vent 14 were nil. Furthermore, even if the hose 5 or the needle 6 were to become clogged, the suction of the pump 10 would still be released through the vent 14. This would prevent a sudden increase in the pressure drop in the hose 13, a problem which, by the sudden unclogging of the hose 5, could result in a sudden reaspiration which could be detrimental to the patient.

As described, it is clear that the device of the present invention provides for the safe and reliable aspiration of the pneumothorax.

It is, of course, possible to connect the induction coil 21 with the pressure gage 26, so as to stabilize the pressure drop at an optimal value indicated by the flow-meter 16.

Likewise, the flow-meter 16 could be replaced by any other type of sensor which is able to measure air flow values and convert them into electrical values.

Having thus described the present invention by way of a detailed description of a preferred embodiment, it will be apparent to those skilled in the art that many modifications may be made from the preferred embodiment without departing from the spirit of the present invention or the scope of the appended claims.

What is claimed as novel is:

1. A device for the aspiration of a pneumothorax through a hollow needle inserted between the ribs of a patient comprising:

hollow needle means for insertion between the ribs of a patient a hose connected to said hollow needle means for flow communication therebetween;

means for suction of a gas from said pneumothorax, said means for suction connected to said hose for flow communication therebetween;

means for sensing the flow rate of said gas drawn from said pneumothorax by said means for suction and for generating an electrical signal which is proportional to said gas flow rate, said means for sensing mounted in said hose between said needle means and said means for suction; and electronic control means responsive to said electrical signal from said means for sensing for calculating and displaying a total volume of gas that has flowed through said hose.

2. The device according to claim 1 wherein said means for sensing comprises:

a float-type flow-meter, the float of said float-type flow-meter floating in the gas flowing through said flow-meter;

a magnetic core connected to said float and movable therewith; and an induction coil surrounding said magnetic core for sensing said flow rate of the gas flowing through said flow-meter by sensing the position of said magnetic core.

3. The device according to claim 2 wherein said float-type flow-meter is connected in series between said hollow needle means and said means for suction.

4. The device according to claim 2 further comprising:

a vent line extending from said hose between said means for suction and said float-type flow-meter, said vent line being exposed at one end to outside atmosphere; and a three-way valve mounted between said hose and said vent line for adjusting said flow rate of gas drawn through said hose and for adjusting said flow rate of gas drawn through said vent line.

5. The device according to claim 4 further comprising:

a low pressure gauge gage for measuring the pressure mounted in said hose between said three-way valve and said float-type flow-meter.

6. The device according to claim 2 further comprising:

a vent line extending from said hose between said means for suction and said float-type flow-meter, said vent line being parallel to said float-type flow-meter and being exposed at one end to outside atmosphere; and a three-way valve mounted between said hose and said vent line for adjusting said flow rate of gas drawn through said hose and for adjusting said flow rate of gas drawn through said vent line.

7. The device according to claim 2 further comprising:

a vent line extending from said hose between said means for suction and said float-type flow-meter, said vent line being parallel to said float-type flow-meter and being exposed at one end to outside atmosphere; and a three-way valve mounted between said hose and said vent line for adjusting said flow rate of gas drawn through said hose and for adjusting said flow rate of gas drawn through said vent line.

8. The device according to claim 1 further comprising:
- a vent line extending from said hose between said means for suction and said means for sensing, said vent line being exposed at one end to outside atmosphere; and
- a three-way valve mounted between said hose and said vent line for adjusting said flow rate of gas drawn through said hose and for adjusting said flow rate of gas drawn through said vent line.

9. The device according to claim 8 further comprising:
- a low pressure gauge for measuring the pressure mounted in said hose between said three-way valve and said means for sensing.

10. The device according to claim 1, wherein said electronic control means further comprises:
- means for stopping the aspiration of gas from said pneumothorax at a predetermined level of total volume of gas drawn through said means for sensing, said means for stopping responsive to said electrical signal from said means for sensing to stop the aspiration of gas.

11. A method of aspirating a pneumothorax comprising the steps of:
- inserting a hollow needle between the ribs of a patient;
- connecting a hose and suction means to said needle;
- aspirating gas from said pneumothorax with said suction means;
- sensing the rate of flow of gas aspirated from said pneumothorax with a sensor;
- generating an electrical signal with said sensor in response to the rate of flow of gas aspirated from said pneumothorax;
- calculating the total volume of gas aspirated from said pneumothorax with an electronic control means; and
- stopping the aspiration of gas from said pneumothorax with said electronic control means when said total volume of gas reaches a predetermined level.

12. The method according to claim 11, wherein said method further comprises, after said step of aspirating, the step of:
- regulating the flow rate of said gas by venting said hose a predetermined amount to atmospheric conditions.

* * * * *

UNITED STATES PATENT AND TRADEMARK OFFICE
CERTIFICATE OF CORRECTION

PATENT NO. : 4,592,741

DATED : June 3, 1986

INVENTOR(S) : Michel Jean Vincent

It is certified that error appears in the above-identified patent and that said Letters Patent is hereby corrected as shown below:

Column 4, line 39 after gas delete a period ".".

Signed and Sealed this

Thirtieth Day of September 1986

[SEAL]

Attest:

DONALD J. QUIGG

Attesting Officer     Commissioner of Patents and Trademarks